(12) United States Patent
Xu et al.

(10) Patent No.: US 11,885,766 B2
(45) Date of Patent: Jan. 30, 2024

(54) PHOTOIONIZATION DETECTOR AND METHOD OF OPERATING SAME

(71) Applicant: Molex, LLC, Lisle, IL (US)

(72) Inventors: Miao Xu, Bolingbrook, IL (US); Wenfeng Peng, North Aurora, IL (US); Mariusz Kloza, Westmont, IL (US); Amram Netanel Afenzer, Skokie, IL (US)

(73) Assignee: Molex, LLC, Lisle, IL (US)

( * ) Notice: Subject to any disclaimer, the term of this patent is extended or adjusted under 35 U.S.C. 154(b) by 0 days.

(21) Appl. No.: 18/107,131

(22) Filed: Feb. 8, 2023

(65) Prior Publication Data

US 2023/0194474 A1   Jun. 22, 2023

Related U.S. Application Data

(63) Continuation of application No. 17/549,182, filed on Dec. 13, 2021, now Pat. No. 11,604,164.

(60) Provisional application No. 63/124,892, filed on Dec. 14, 2020.

(51) Int. Cl.
   *G01N 27/66* (2006.01)
   *G01N 33/00* (2006.01)

(52) U.S. Cl.
   CPC ......... *G01N 27/66* (2013.01); *G01N 33/0047* (2013.01)

(58) Field of Classification Search
   CPC .......................... G01N 27/66; G01N 33/0047
   USPC ........................................................ 324/464
   See application file for complete search history.

(56) References Cited

U.S. PATENT DOCUMENTS

| 6,313,638 | B1 * | 11/2001 | Sun ........................ | H01J 41/02 324/464 |
| 6,646,444 | B2 | 11/2003 | Dolgov et al. | |
| 7,046,012 | B2 * | 5/2006 | Dean ...................... | G01N 27/62 324/459 |
| 7,821,270 | B2 * | 10/2010 | Stockdale .............. | G01N 27/66 439/111 |
| 2016/0334381 | A1 | 11/2016 | King-Smith et al. | |
| 2020/0025716 | A1 | 1/2020 | Chen et al. | |

(Continued)

FOREIGN PATENT DOCUMENTS

| CA | 2299365 A1 * | 8/1998 |
| CA | 2299365 A1 | 2/1999 |

(Continued)

OTHER PUBLICATIONS

International Search Report and Written opinion received for PCT application No. PCT/IB2021/061667, dated Mar. 15, 2022, 6 pages.

(Continued)

*Primary Examiner* — Christopher P McAndrew

(57) ABSTRACT

An electrode stack assembly includes an electrically insulative substrate having a cavity therethrough extending, a first counter electrode on a top surface thereof and extending through the substrate, a second sensing electrode on a bottom surface thereof and extending through the substrate, and a third electrode having a top body portion on a top of the substrate, a bottom body portion on a bottom of the substrate, and a coupling pin passing through the substrate and electrically coupling the top and bottom body portions. The third electrode electrically separates the pin of the sensing electrode from the counter electrode.

20 Claims, 12 Drawing Sheets

(56) References Cited

U.S. PATENT DOCUMENTS

2020/0103366 A1\* 4/2020 Umasankar ........ G01N 27/4065
2020/0333292 A1   10/2020 Su et al.

FOREIGN PATENT DOCUMENTS

| EP | 1998171  | A2 |   | 12/2008 |
|----|----------|----|---|---------|
| EP | 2988122  | A1 | \* | 2/2016 |
| EP | 2988122  | A1 |   | 2/2016 |
| EP | 2458375  | B1 | \* | 8/2017 |
| EP | 2458375  | B1 |   | 8/2017 |
| GB | 2469803  | A  | \* | 11/2010 |
| GB | 2469803  | A  |   | 11/2010 |
| GB | 2527867  | A  | \* | 1/2016 |
| GB | 2527867  | A  |   | 1/2016 |
| JP | 3876554  | B2 | \* | 1/2007 |
| JP | 3876554  | B2 |   | 1/2007 |

OTHER PUBLICATIONS

International Preliminary Report on Patentability received for PCT application No. PCT/IB2021/061667, dated Jun. 29, 2023, 05 Pages.

\* cited by examiner

PHOTOIONIZATION DETECTOR AND METHOD OF OPERATING SAME

RELATED APPLICATIONS

This continuation patent application claims the benefit of priority to U.S. patent application Ser. No. 17/549,182, filed Dec. 13, 2021, which claims priority to U.S. Provisional Patent Application No. 63/124,892, filed Dec. 14, 2020. All of the aforementioned are herein incorporated herein by reference in their entireties.

FIELD OF THE DISCLOSURE

This disclosure relates to a photoionization detector for the detection of gas or vapor molecules with photoionization technology and the general operation of such a photoionization detector. More specifically, this disclosure provides a configuration and approach to minimize the impact of environment humidity and to increase the photoionization detector reliability for both indoor and outdoor applications.

DESCRIPTION OF RELATED ART

The concern for clean living, working and the industrial environment has increased over the recent decades. Various methods and instruments have been developed to address these concerns through accurate measurement of contaminations or pollution concentration, especially for gas contaminations. Volatile organic compounds (VOCs) remain challenging because of the colorlessness, low odor, and high reduction-oxidation reaction (as known as redox) potential in general. Photoionization detectors ("PIDs") are one of the successful solutions to tackle this difficulty because they use high energy photons to break the VOC molecules into ions and free electrons (thereby generating a plasma) and accurately measuring the plasma current which typically correlates to the VOC concentration. The measurement range is typically 0.01-10,000 parts per million (ppm), as compared to the measurement range of other devices, e.g., 0.5-50,000 ppm for flame ionization detectors ("FIDs"), 100-50,000 ppm for infrared (IR) analyzers, 1-10,000 ppm for metal oxide semiconductors ("MOS"), and 200-50,000 ppm for catalytic oxidation bead combustible gas (LEL) sensors.

The general working principle of PIDs is the measurement of ionic current which is related to the gas concentration when the gas molecules are ionized by high energy ultraviolet (UV) light. The electrons are moved into an electrical field between two electrodes and are collected on the positive electrode to form a current which is generally proportional to the gas concentration. One key part of the PID is the lamp which is usually filled with a low-pressure inert gas that emits photons in the vacuum-ultraviolet region. Salt crystals (e.g., $MgF_2$, LiF, $CaF_2$, $BaF_2$) are used as windows because common silica glasses do not transmit the short wavelength light required to ionize target VOCs. Examples of inert fill gases are Ar, Ke, $H_2$, or Xe. Another key part of the PID is the electrodes, which collect the plasma/ionic current in a high voltage electric field (applied on both the counter and sensing electrodes). Usually, the electrons are collected by the sensing electrode (anode, positively charged) and the resultant cations are collected by the counter electrode (cathode, negatively charged).

Ideally, the current from the sensing electrode is proportional to the gas concentration. However, in the field, the surrounding temperature and humidity of the PID varies, which might result in a formation of condensation or mist outside or even inside of the PID. This condensation might lead to a false reading and misinterpretation of the current VOC level. The false reading might come from a leak current between the counter electrode and the sensing electrode, which is due to the formation of a conducting path as a result of condensation and other possibilities. Thus, the design to overcome such challenges like condensation or mist is critical for a robust PID. One method toward overcoming this issue is to use filters, but such method has generally proven to be difficult to implement and/or is not achieving the desired performance.

Another method, which has had general success in the marketplace, and developed by Ion Science Limited, is to use another electrode, for example, a fence electrode, that is generally disposed within an ionization chamber between the sensing electrode and the counter electrode to "block" the leak current from reaching the sensing electrode, thus essentially making the leak current zero or close to zero. This method is generally described and illustrated in U.S. Pat. No. 7,046,012. More specifically, as described in U.S. Pat. No. 7,046,012, the sensing electrode is positioned at one end of the ionization chamber proximate to the lamp window while the counter electrode is positioned at an opposite end of the ionization chamber, distal from the lamp window, and the fence electrode is positioned within the ionization chamber between the sensing electrode and the counter electrode. In practice, electrical potential is applied to each of the electrodes with the electrical potential applied to the fence electrode being equal to, or substantially equal to, the electrical potential applied to the sensing electrode, with such electrical potential being different from the electrical potential applied to the counter electrode, such that a voltage differential is defined between the sensing electrode and the counter electrode. With the electrical potentials applied, the current from the counter electrode to the sensing electrode is measured, which is essentially equal to the plasma/ionic current.

The foregoing method, however, has some disadvantages. More specifically, the foregoing method only "blocks" the leak current within the ionization chamber. However, based on testing, it has been determined that a larger percentage of the leak current occurs outside of the ionization chamber, namely on a surface of the substrate(s) (that forms the ionization chamber) that faces the gas inlet.

As a result of the foregoing, certain individuals would appreciate further improvements in PIDs and the operation of same.

BRIEF SUMMARY

Accordingly, the present disclosure provides an electrode stack assembly includes an electrically insulative substrate having a cavity therethrough extending, a first counter electrode on a top surface thereof and extending through the substrate, a second sensing electrode on a bottom surface thereof and extending through the substrate, and a third electrode having a top body portion on a top of the substrate, a bottom body portion on a bottom of the substrate, and a coupling pin passing through the substrate and electrically coupling the top and bottom body portions. The third electrode electrically separates the pin of the sensing electrode from the counter electrode. In a first embodiment, the top body portion encircles the pin of the pin of the sensing electrode, and is spaced therefrom, and the bottom body portion encircles the body of the sensing electrode, and is spaced therefrom. In a second embodiment, the top body portion encircles the body of the counter electrode, and is spaced therefrom, and the bottom body portion encircles the pin of the sensing electrode, and is spaced therefrom. In a third embodiment, the top body portion encircles the pin of the sensing electrode, and is spaced therefrom, and the bottom body portion encircles the pin of the counter electrode, and is spaced therefrom.

A method of operating a photoionization detector is also provided. In a first embodiment of the method, the following is provided: applying a first electric potential to a counter electrode on a top surface of an electrically insulative substrate, applying a second electric potential to a sensing electrode on a bottom surface of the insulative substrate, applying a third electric potential to an electrode having a top body portion on the top surface of the substrate and a bottom body portion on the bottom surface of the substrate, the top and bottom body portions being electrically coupled together, and the top and bottom body portions separating a current path of the counter electrode from a current path of the sensing electrode, wherein the first and third electric potentials are the same or generally the same, and the second electric potential is generally higher than the first potential, and ionizing gas in a cavity of the insulative substrate. In a second embodiment of the method, the following is provided: applying a first electric potential to a counter electrode on a top surface of an electrically insulative substrate, applying a second electric potential to a sensing electrode on a bottom surface of the insulative substrate, applying a third electric potential to an electrode having a top body portion on the top surface of the substrate and a bottom body portion on the bottom surface of the substrate, the top and bottom body portions being electrically coupled together, and the top and bottom body portions separating a current path of the counter electrode from a current path of the sensing electrode, wherein the second and third electric potentials are the same or generally the same, and the second electric potential is generally higher than the first potential, and ionizing gas in a cavity of the insulative substrate.

BRIEF DESCRIPTION OF THE DRAWINGS

The present disclosure is illustrated by way of example, and not limited, in the accompanying figures in which like reference numerals indicate similar elements and in which.

DETAILED DESCRIPTION

Figure 1:
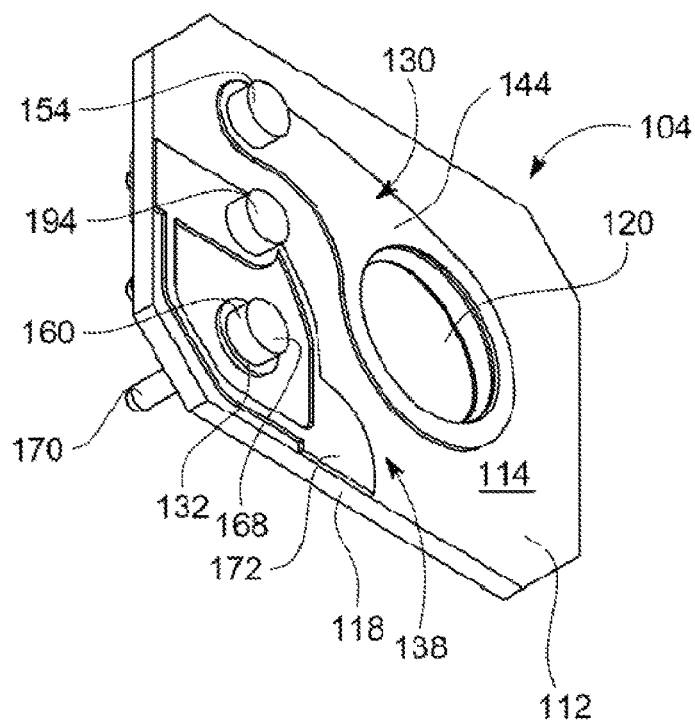
FIG. 1 depicts a top perspective view of an electrode stack assembly according to a first embodiment.

While the disclosure may be susceptible to embodiment in different forms, there is shown in the drawings, and herein will be described in detail, specific embodiments with the understanding that the present disclosure is to be considered an exemplification of the principles of the disclosure, and is not intended to limit the disclosure to that as illustrated and described herein. Therefore, unless otherwise noted, features disclosed herein may be combined to form additional combinations that were not otherwise shown for purposes of brevity. It will be further appreciated that in some embodiments, one or more elements illustrated by way of example in a drawing(s) may be eliminated and/or substituted with alternative elements within the scope of the disclosure.

Contrary to the prior art PIDs and operation methods used as described above, the current disclosure handles the issue with alternative configurations and methods, which alternative configurations and methods not only provide a plasma/ionic current, but also provides further advantages as will be explained in further detail hereinbelow. In the PIDs of the designs described in detail below, and the associated methods of use: (1) an electrode is partially located around the sensing electrode (which is understood to be the primary pathway of surface leak current), but not located in/around the ionization chamber; (2) an air-gapped multi-layer electrode structure may be provided which assists in preventing the leak current leaking across layers instead of using a metallic layer to "block" the leak current; and (3) the surface of metal layer is not coated with dielectric material.

The leak current between the counter electrode and the sensing electrode has several possibly pathways in the electrode structure: (1) between electrode layers (if electrode contains multiple layers); (2) on the surface of the same electrode layer; and/or (3) on the edge of the same layer. There are also two general methods to alleviate the impact of the leak current, either to block or measure the leak current. Both methods rely on rational designs on the leak current pathways to either stop or collect the leak current. Herein, a design/method uses a combined with spaced electrode layers to limit the leak current within the same electrode layer to block/compensate the leak current and afford a humidity resistant PID electrode.

The leak current on the electrode surface will be stopped or collected by a guard/auxiliary electrode to reduce/compensate the impact of the humidity-introduced leak current. There are three major considerations for this design: (1) the humidity reaches the surfaces of electrode layers and build a condensation water trace on surfaces, which will provide a conductive pathway once enough ions are dissolved into this water trace; (2) the counter electrode and the sensing electrode have the longest edge on the outer side of the counter electrode or the sensing electrode, which yields the highest possibility of building a conductive path; and (3) the guard/auxiliary electrode encircles the counter electrode/ sensing electrode and has a potential equal or close to the sensing electrode (block mode) or to the counter electrode (compensation mode) which helps assure an effective reduction/compensation of the leak current. The design described herein also provides for the counter electrode to be on one side of a substrate, and the sensing electrode on the other side of the substrate, which greatly simplifies the production process and makes the design cost-effective and mass reproducible.

Additional designs/methods may be used to prevent the leak current, if two or more layers of substrates (on which the electrode are attached) are used. For instance, substrates may be configured to contact each other only with pins/other mechanical structures to create an air gap in the ionization chamber between layers and minimize the leak current across two layers. With the air-gapped electrode substrate, the leak current will be limited within the same electrode substrate layer and not travel to the other electrode substrate layer. In addition, pin mounting holes are designed to be slightly larger than the diameter of the pins to create a small air gap between each pin and the electrode substrate to minimize the current leaking on the supporting substrate.

The guard/auxiliary electrode encircles around the counter electrode or the sensing electrode on the same side of the sensing electrode and the counter electrode. The potential of the guard/auxiliary electrode will be held at or close to the potential of the sensing electrode (block mode) or the counter electrode (compensation mode). Multiple guard/auxiliary electrodes/pins may be provided on one surface. In the block mode, the leak current is stopped by the electrode functioning as a guard electrode, and the measured current is considered as the true plasma current, which correlates to the gas concentration. In the compensation mode, the leak current is subtracted from the total current to afford the true plasma current. The guard/auxiliary electrode is not provided in the inner surface of the electrode layers (e.g., in/around the ionization chamber) since the leak current from these two surfaces is minimal (potential is only applied around the mounting pins).

A first embodiment of a photoionization detector ("PID") 100 is shown in FIGS. 1-6. A second embodiment of a photoionization detector ("PID") 200 is shown in FIGS. 7-12. A third embodiment of a photoionization detector ("PID") 300 is shown in FIGS. 13-18.

Attention is directed to FIGS. 1-6 and the first embodiment of the PID 100. PID 100 includes a lamp assembly 102 and an electrode stack assembly 104 which are operatively associated with one another. The PID 100 and the electrode stack assembly 104 are intended to be operated in the block mode or the compensation mode.

Figure 6:
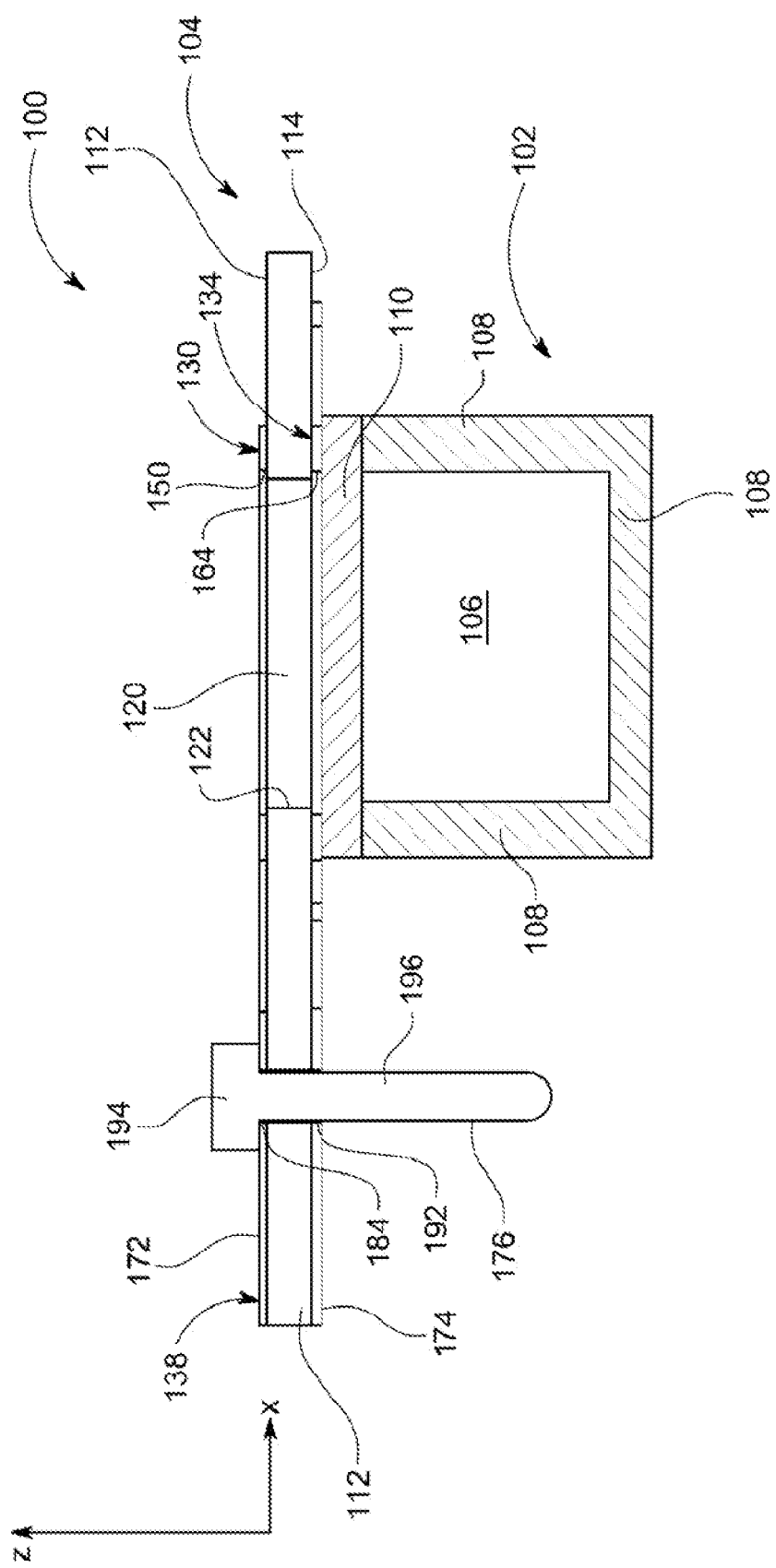
FIG. 6 depicts a cross-sectional view of a photoionization detector including the electrode stack assembly of FIG. 1.

As illustrated in FIG. 6, the lamp assembly 102 includes a light chamber 106 defined by one or more walls 108. A window 110 is provided at an end of the walls 108 (illustrated in FIG. 6 as being at a top end of the walls 108). The walls 108 are preferably formed of glass and the window 110 is preferably formed of salt crystals (e.g., $MgF_2$, LiF, $CaF_2$, $BaF_2$) as they allow for the transmission of the vacuum UV light required to ionize target compounds. The light chamber 106 may contain a low-pressure inert gas such as Ar, Ke, $H_2$, or Xe, as is known to those skilled in the art.

Figure 5:
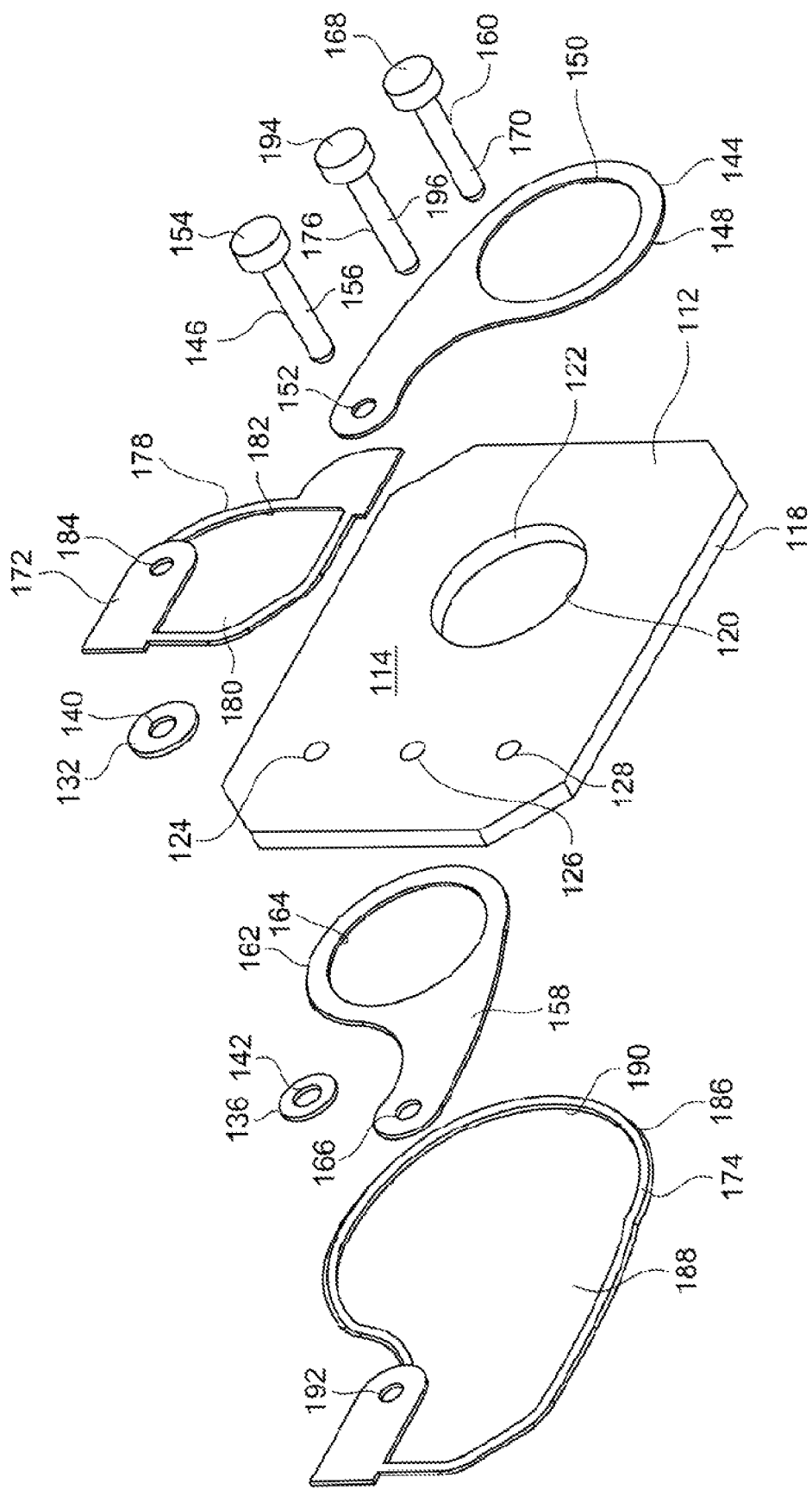
FIG. 5 depicts an exploded perspective view of the electrode stack assembly.

The electrode stack assembly 104 includes a substrate 112 that is preferably formed of a waterproof/water repellant, electrically insulative material, such as that commonly sold under the trademark TEFLON. The substrate 112 has a top surface 114, a bottom surface 116 and one or more outer surfaces 118 which connect the top surface 114 to the bottom surface 116. The one or more outer surfaces 118 extend in a first direction (for example along a z-axis). The substrate 112 has a cavity 120 provided therethrough from the top surface 114 to the bottom surface 116. The cavity 120 functions as an ionization gas chamber (as will be discussed in further detail hereinbelow) that is defined by one or more walls 122 (depicted in the drawings as a single, circular-shaped wall which extends in the first direction). It should be noted that while the cavity 120 is illustrated as a single hole, that the cavity 120 could alternatively be configured as a plurality of separate holes (formed in a pattern or randomly). As shown in FIG. 5, the substrate 112 has three pin mounting holes 124, 126, 128 provided therethrough from the top surface 114 to the bottom surface 116. The pin mounting holes 124, 126, 128 are defined by one or more walls. The centers of the pin mounting holes 124, 126, 128 may be in alignment with each other in a second direction which is perpendicular to the first direction (for example along a y-axis) and the center of the pin mounting hole 126 and the center of the cavity 120 may be in alignment with each other in a third direction perpendicular to the first and second directions (for example along an x-axis). While a single substrate 112 is shown in the drawings, it is to be understood that multiple substrates could be provided that have common configurations, where the substrates are separated from one another and those portions identified as being associated with the top surface of the substrate are associated with the top surface of an top substrate and those portions identified as being associated with the bottom surface of the substrate are associated with the bottom surface of a bottom substrate.

The electrode stack assembly 104 includes a first electrode 130 which forms a counter electrode, an optional top contact pad 132, a second electrode 134 which forms a sensing electrode, an optional bottom contact pad 136, and a third electrode 138 which in one mode provides a guard electrode and another mode provides an auxiliary electrode.

Figure 3:
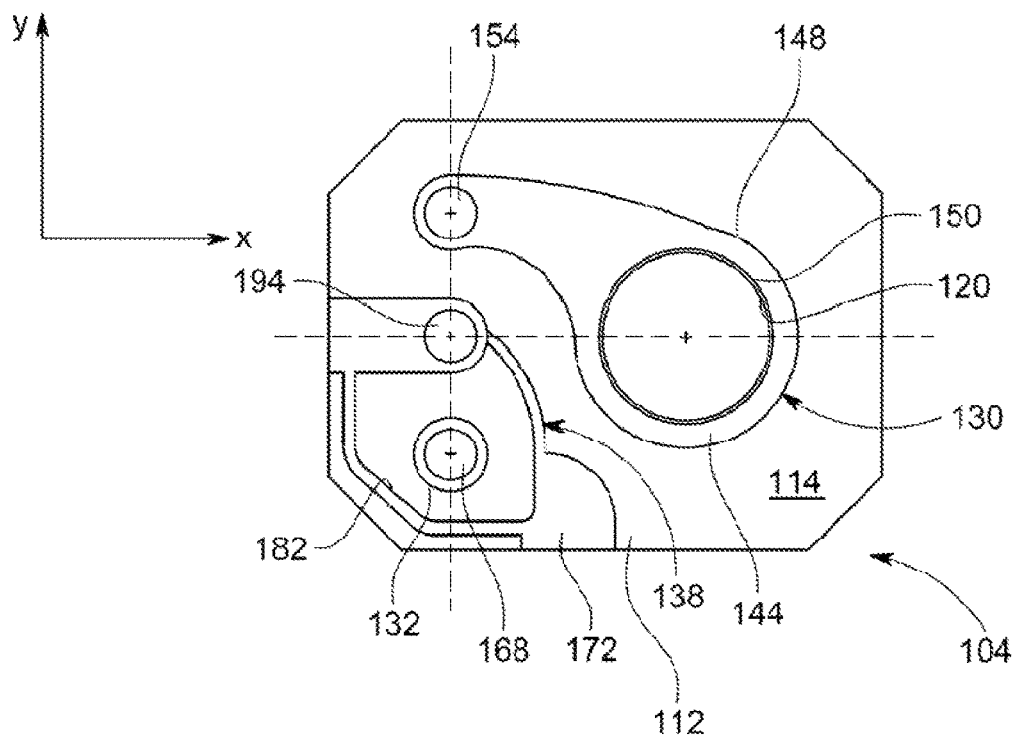
FIG. 3 depicts a top plan view of the electrode stack assembly.

As best illustrated in FIGS. 1 and 3, the top contact pad 132 (if provided) is provided on the top surface 114 of the substrate 112 and has a pin mounting hole 140 provided therethrough. The bottom surface of the top contact pad 132 (if provided) is further positioned on the top surface 114 of the substrate 112 such that the pin mounting hole 140 is in alignment with the pin mounting hole 128 through the substrate 112. The diameter of the pin mounting hole 140 is sized to generally match the diameter of the pin mounting hole 128.

Figure 2:
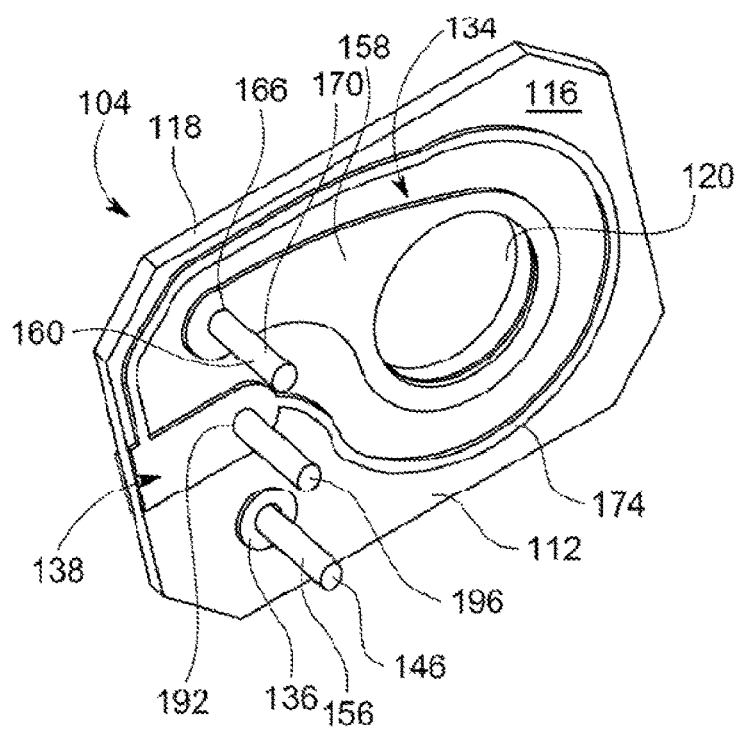
FIG. 2 depicts a bottom perspective view of the electrode stack assembly.
Figure 4:
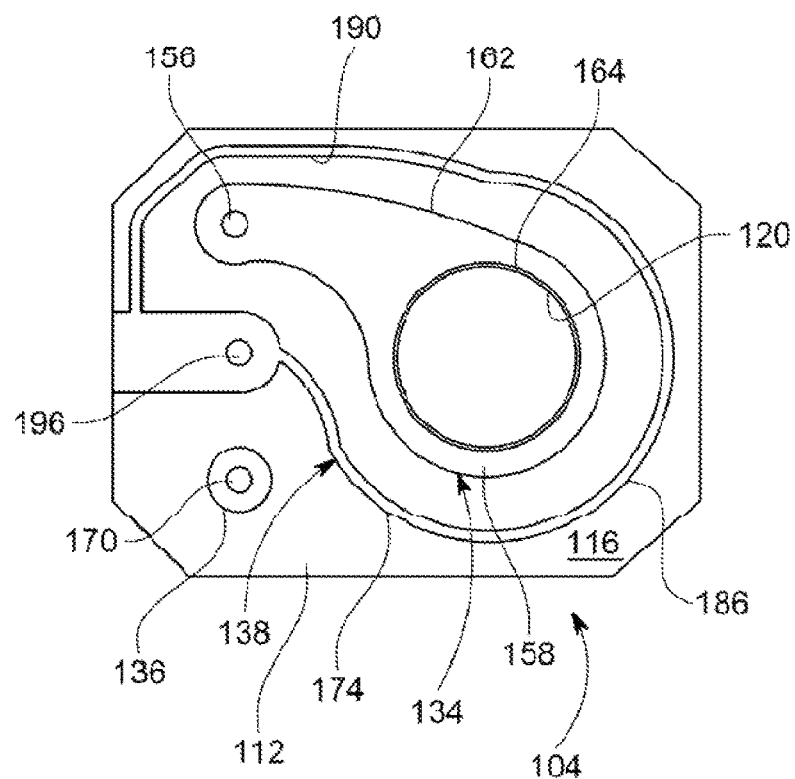
FIG. 4 depicts a bottom plan view of the electrode stack assembly.

As best illustrated in FIGS. 2 and 4, the bottom contact pad 136 (if provided) is provided on the bottom surface 116 of the substrate 112 and has a pin mounting hole 142 provided therethrough. The top surface of the bottom contact pad 136 is further positioned on the bottom surface 116 of the substrate 112 such that the pin mounting hole 142 of the bottom contact pad 136 is in alignment with the pin mounting hole 124 through the substrate 112. The diameter of the pin mounting hole 142 of the bottom contact pad 136 is sized to generally match the diameter of the pin mounting hole 124.

As best illustrated in FIGS. 1 and 3, the counter electrode 130 is provided on the top surface 114 of the substrate 112. The counter electrode 130 includes a body 144 and a pin 146 extending therefrom. The body 144 has a top surface, a bottom surface and a continuous outer edge 148 extending between the top and bottom surfaces. An opening 150 and a pin mounting hole 152 are provided through the body 144, are spaced from each other and are spaced from the outer edge 148, and extend from the top surface to the bottom surface.

The bottom surface of the counter electrode 130 is positioned on the top surface 114 of the substrate 112 such that the opening 150 is in alignment with the cavity 120 through the substrate 112, and such that the pin mounting hole 152 is in alignment with the pin mounting hole 124 through the substrate 112. The diameter of the opening 150 is sized to generally match the diameter of the cavity 120, and the diameter of the pin mounting hole 152 is sized to generally match the diameter of the pin mounting hole 124. The pin 146 has an enlarged head portion 154 that preferably has an outer diameter that is larger than a diameter of the pin mounting hole 124, and an elongated shaft 156 extending therefrom. The enlarged head portion 154 of the pin 146 rests on the top surface of the body 144, and the shaft 156 extends through the pin mounting hole 152 of the body 144, through the pin mounting hole 124 of the substrate 112, through the pin mounting hole 142 of the bottom contact pad 136 (if provided), and extends from the bottom surface of the counter electrode 130. The pin 146 is preferably held in place by known means, e.g., soldering to the body 144 and, to the bottom contact pad 136 (if provided). While the body 144 and the pin 146 are described as two separate components permanently mated together, in an embodiment, the body 144 and the pin 146 are integrally formed as one piece.

As best illustrated in FIGS. 1 and 3, the sensing electrode 134 is provided on the bottom surface 116 of the substrate 112. The sensing electrode 134 includes a body 158 and a pin 160 extending therefrom. The body 158 has a top surface, a bottom surface and a continuous outer edge 162 extending between the top and bottom surfaces. An opening 164 and a pin mounting hole 166 are provided through the body 158, are spaced from each other and are spaced from the outer edge 162, and extend from the top surface to the bottom surface.

The top surface of the sensing electrode 134 is positioned on the bottom surface 116 of the substrate 112 such that the opening 164 is in alignment with the cavity 120 through the substrate 112 and such that the pin mounting hole 166 is in alignment with the pin mounting hole 128 through the substrate 112. The diameter of the opening 164 is sized to generally match the diameter of the cavity 120, and the diameter of the pin mounting hole 166 is sized to generally match the diameter of the pin mounting hole 128. The pin 160 has an enlarged head portion 168 that preferably has an outer diameter that is larger than a diameter of the pin mounting hole 128, and an elongated shaft 170 extending therefrom. The enlarged head portion 168 of the pin 160 rests on the top surface of the top contact pad 132 (if provided; if the top contact pad 132 is not provided then the head portion 168 rests on the top surface 114 of the substrate 112), and the shaft 170 extends through the top contact pad 132 (if provided), through the pin mounting hole 128 of the substrate 112, through the pin mounting hole 166 of the body 158, and extends from the bottom surface of the body 158. The pin 160 is preferably held in place by known means, e.g., soldering to the body 158 and, to the top contact pad 132 (if provided). While the body 158 and the pin 160 are described as two separate components permanently mated together, in an embodiment, the body 158 and the pin 160 are integrally formed as one piece.

The third electrode 138 includes a top body portion 172, a bottom body portion 174 which are coupled together by a coupling pin 176.

The top body portion 172 has a top surface, a bottom surface and a continuous outer edge 178 extending between the top and bottom surfaces. An opening 180 formed by a continuous wall 182 and a pin mounting hole 184 are provided through the top body portion 172, are spaced from each other and are spaced from the outer edge 178, and extend from the top surface to the bottom surface. The bottom surface of the top body portion 172 is provided on the top surface 114 of the substrate 112 such that the pin mounting hole 184 is in alignment with the pin mounting hole 126 through the substrate 112. The top contact pad 132 (if provided) and the enlarged head portion 168 of the pin 160 are encircled within, but separated from, the wall 182. The pin mounting hole 184 is sized to generally match the diameter of the pin mounting hole 126.

The bottom body portion 174 has a top surface, a bottom surface and a continuous outer edge 186 extending between the top and bottom surfaces. An opening 188 formed by a continuous wall 190 and a pin mounting hole 192 are provided through the bottom body portion 174, are spaced from each other and are spaced from the outer edge 186, and extend from the top surface to the bottom surface. The top surface of the bottom body portion 174 is provided on the bottom surface 116 of the substrate 112 such that the pin mounting hole 192 is in alignment with the pin mounting hole 126 through the substrate 112. The sensing electrode 134 is encircled within, but separated from, the wall 190. The diameter of the pin mounting hole 192 is sized to generally match the diameter of the pin mounting hole 126.

The coupling pin 176 has an enlarged head portion 194 that preferably has an outer diameter that is larger than a diameter of the pin mounting hole 126, and an elongated shaft 196 extending therefrom. The enlarged head portion 194 of the coupling pin 176 rests on the top surface of the top body portion 172, and the shaft 196 extends through the pin mounting hole 184 of the top body portion 172, through the pin mounting hole 126 of the substrate 112, through the pin mounting hole 192 of the bottom body portion 174, and the shaft 196 extends from the bottom surface of the bottom body portion 174. Coupling pin 176 is preferably held in place by known means, e.g., soldering to the top body portion 172 and to the bottom body portion 174.

The enlarged head portion 154, 168, 194 of each pin 146, 160, 176 preferably has an outer diameter that is larger than a diameter of the pin mounting hole 124, 128, 126. The elongated shafts 156, 170 of pins 146, 160 preferably has an outer diameter that is smaller than the diameter of the pin mounting hole 124, 128 to create a small air gap between each pin 146, 160 and the substrate 112 to minimize the current leaking on the substrate 112. The elongated shaft 196 of the pin 176 may have an outer diameter that is substantially the same as the diameter of the pin mounting hole 126.

In use, an electric potential is applied from below the substrate 112 to the pin 146 which applies electric potential to the body 144 of the counter electrode 130 and to the bottom contact pad 136 (if provided), an electric potential is applied from below the substrate 112 to the pin 160 which applies electric potential to the body 158 of the sensing electrode 134 and to the top contact pad 132 (if provided), and an electric potential is applied from below the substrate 112 to the coupling pin 176 which applies electric potential to the top body portion 172 and to the bottom body portion 174. When the PID 100 is operating in block mode, the third electrode 138 is held at or close to (within 20 Volts) the potential of the sensing electrode 134. As a result, the third electrode 138 acts as a guard electrode. In the block mode, the leak current is stopped by the guard electrode 138, and the measured current is considered as the true plasma current, which correlates to the gas concentration. When the PID 100 is operating in compensation mode, the third electrode 138 is held at or close to (within 20 Volts) the potential of the counter electrode 130. As a result, the third electrode 138 acts as an auxiliary electrode. In the compensation mode, the leak current is subtracted from the total current to afford the true plasma current.

The sensing electrode 134 collects the electrons from the ionized gas in the ionization chamber formed by cavity 120. The top body portion 172 electrically separates the pin 160 from the counter electrode 130, and the bottom body portion 174 electrically separates the pin 160 from the counter electrode 130, thereby substantially eliminating the primary pathway of surface leak current. The third electrode 138 separates a current path of the counter electrode 130 from a current path of the sensing electrode 134.

Attention is directed to the second embodiment of the PID 200 shown in FIGS. 7-12. PID 200 includes the lamp assembly 102 and an electrode stack assembly 204 which are operatively associated with one another. The PID 200 and the electrode stack assembly 204 are intended to be operated in either the block mode or the compensation mode. The lamp assembly 102 of PID 200 is identical to the lamp assembly 102 of PID 100 and, therefore, for brevity purposes, will not be described again in detail.

The electrode stack assembly 204 includes a substrate 212 that is identically formed to the substrate 112, a counter electrode 230 identically formed to the counter electrode 130, an optional top contact pad 232 identically formed to the top contact pad 132, a sensing electrode 234 identically formed to the sensing electrode 134, a bottom contact pad 236 (if provided) identically formed to the bottom contact pad 136 (if provided), and a third electrode 238 which in one mode forms a guard electrode and another mode provides an auxiliary electrode. The counter electrode 230 and top contact pad 232 (if provided) are provided on the top surface 214 of the substrate 212 in an identical manner to that of the first embodiment. Likewise, the sensing electrode 234 and bottom contact pad 236 (if provided) are provided on the bottom surface 216 of the substrate 212 in an identical manner to that of the first embodiment. The pin 246 extends through the body 244 of the counter electrode 230, the substrate 212 and the bottom contact pad 236 (if provided) in the same manner as the first embodiment, and is coupled to the components in the same manner (or may integrally formed as part of the counter electrode 230). The pin 260 extends through the top contact pad 232 (if provided), the substrate 212, and the body 258 of the sensing electrode 234 in the same manner as the first embodiment, and is coupled to the components in the same manner (or may integrally formed as part of the sensing electrode 234). As such, the specifics are not repeated herein and like element are denoted with like reference numerals in the two hundreds.

The third electrode 238 includes a top body portion 272 and a bottom body portion 274 which are coupled together by a pin 276.

Figure 7:
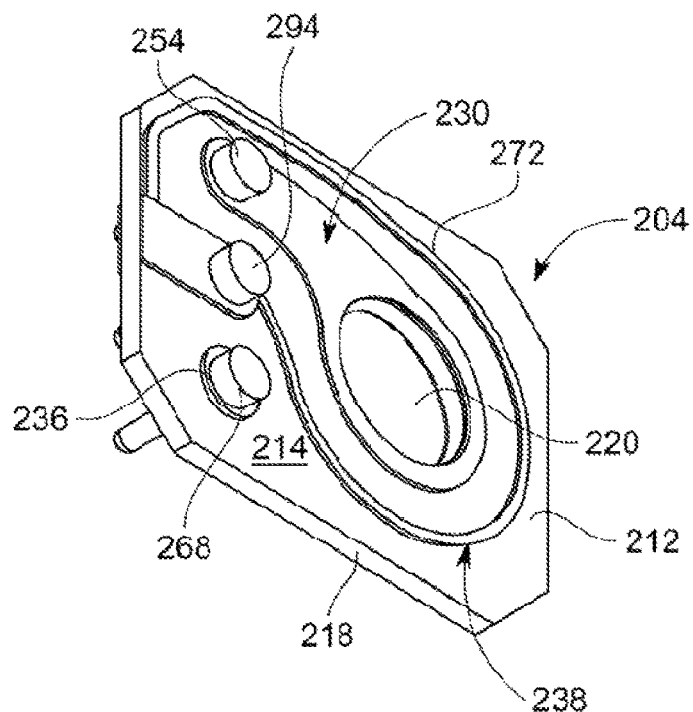
FIG. 7 depicts a top perspective view of an electrode stack assembly according to a second embodiment.
Figure 8:
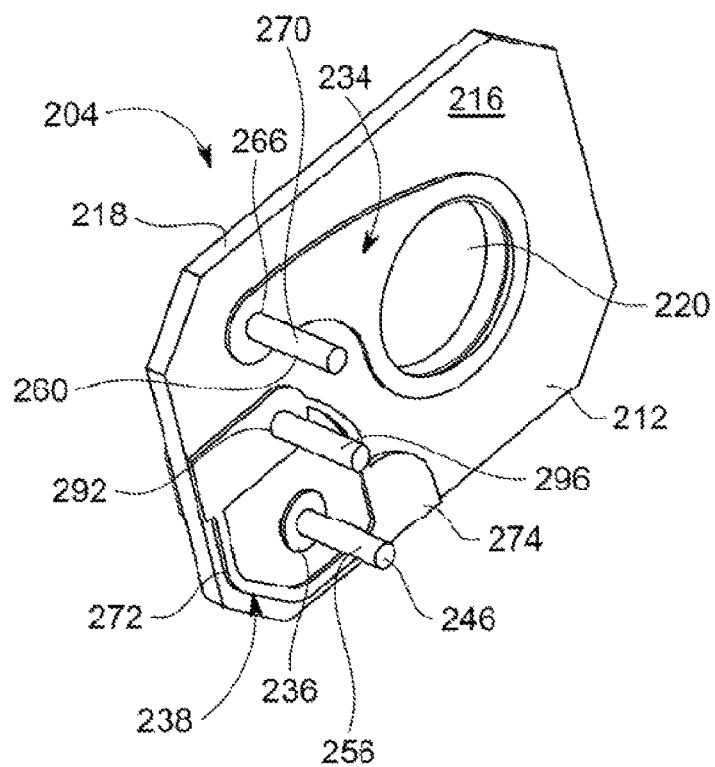
FIG. 8 depicts a bottom perspective view of the electrode stack assembly of FIG. 7.
Figure 9:
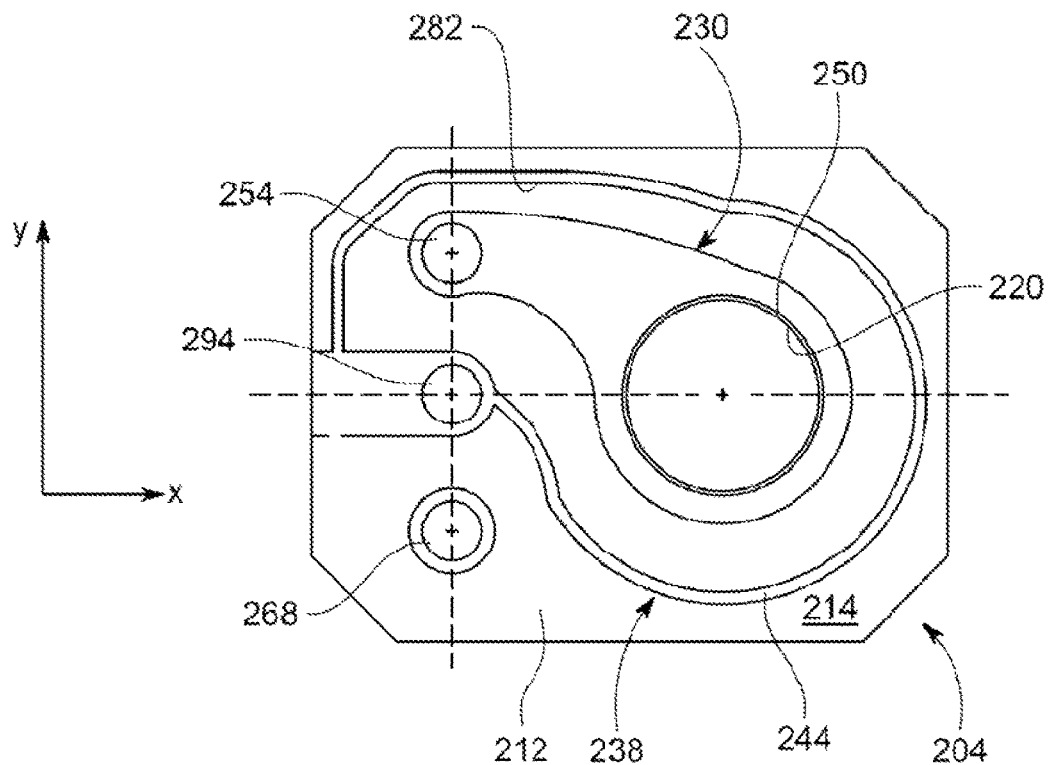
FIG. 9 depicts a top plan view of the electrode stack assembly of FIG. 7.
Figure 10:
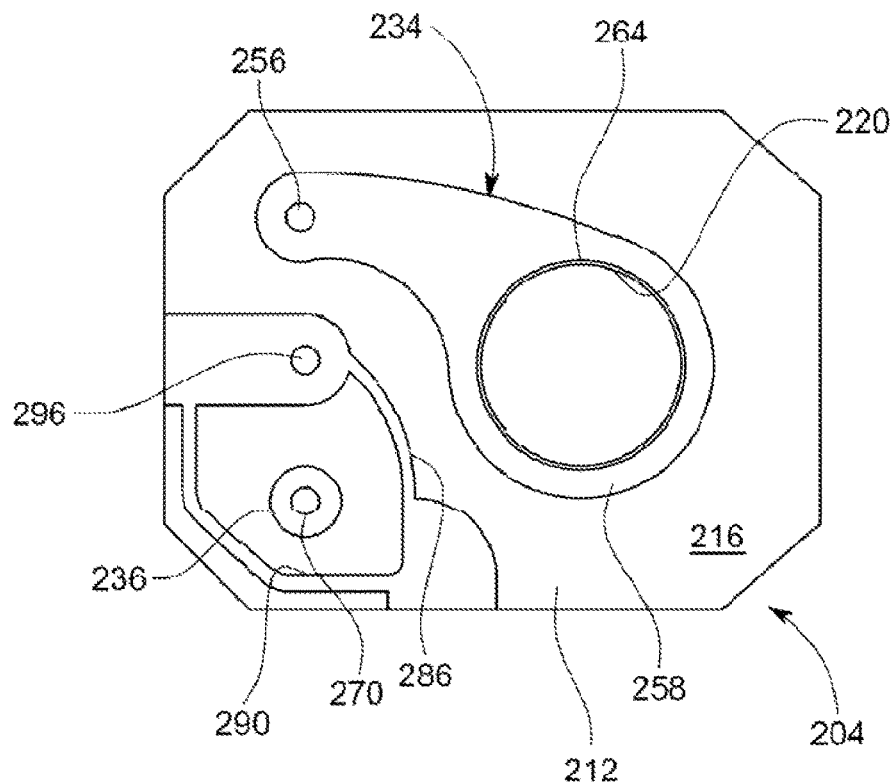
FIG. 10 depicts a bottom plan view of the electrode stack assembly of FIG. 7.
Figure 11:
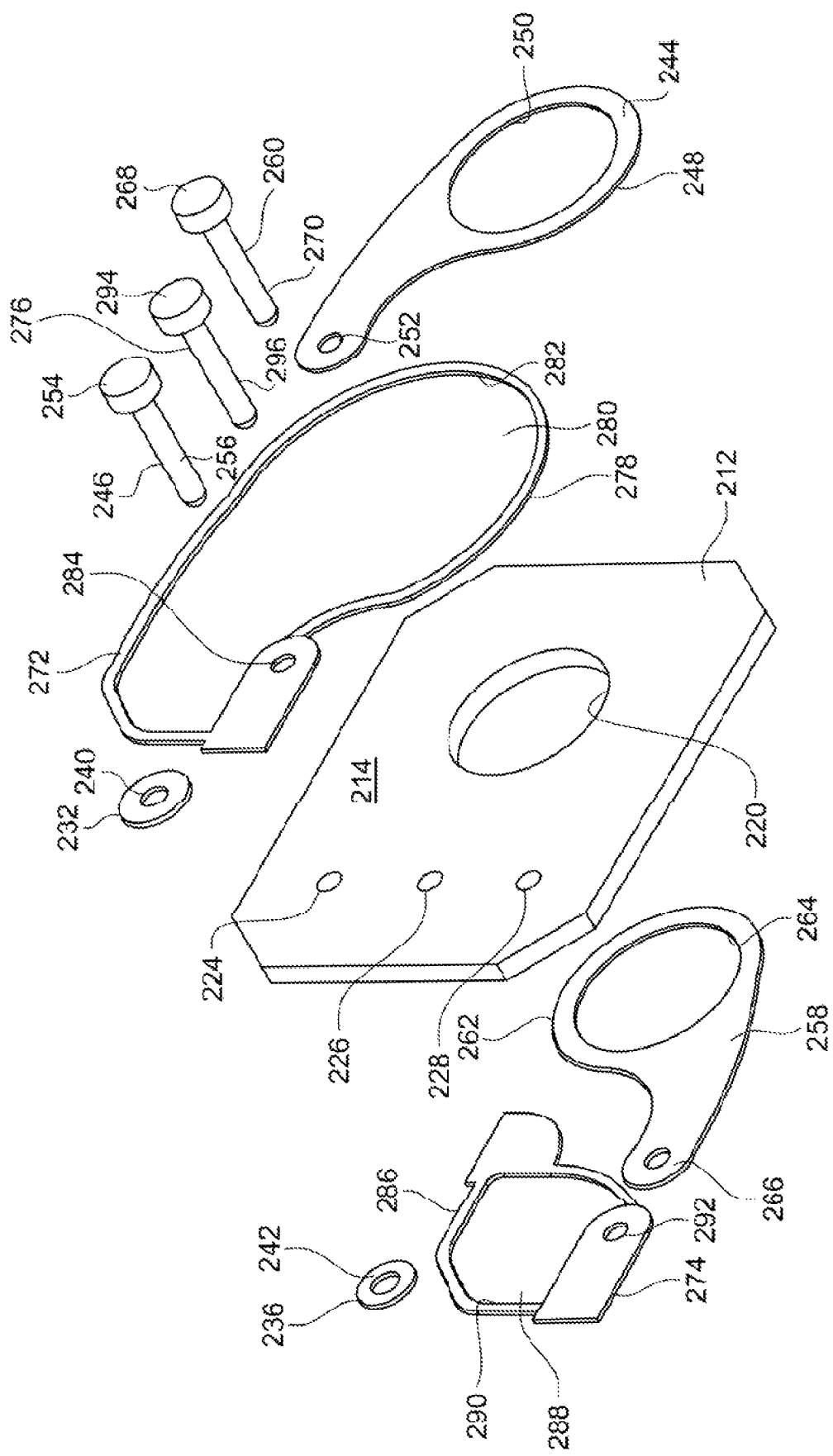
FIG. 11 depicts an exploded perspective view of the electrode stack assembly of FIG. 7.
Figure 12:
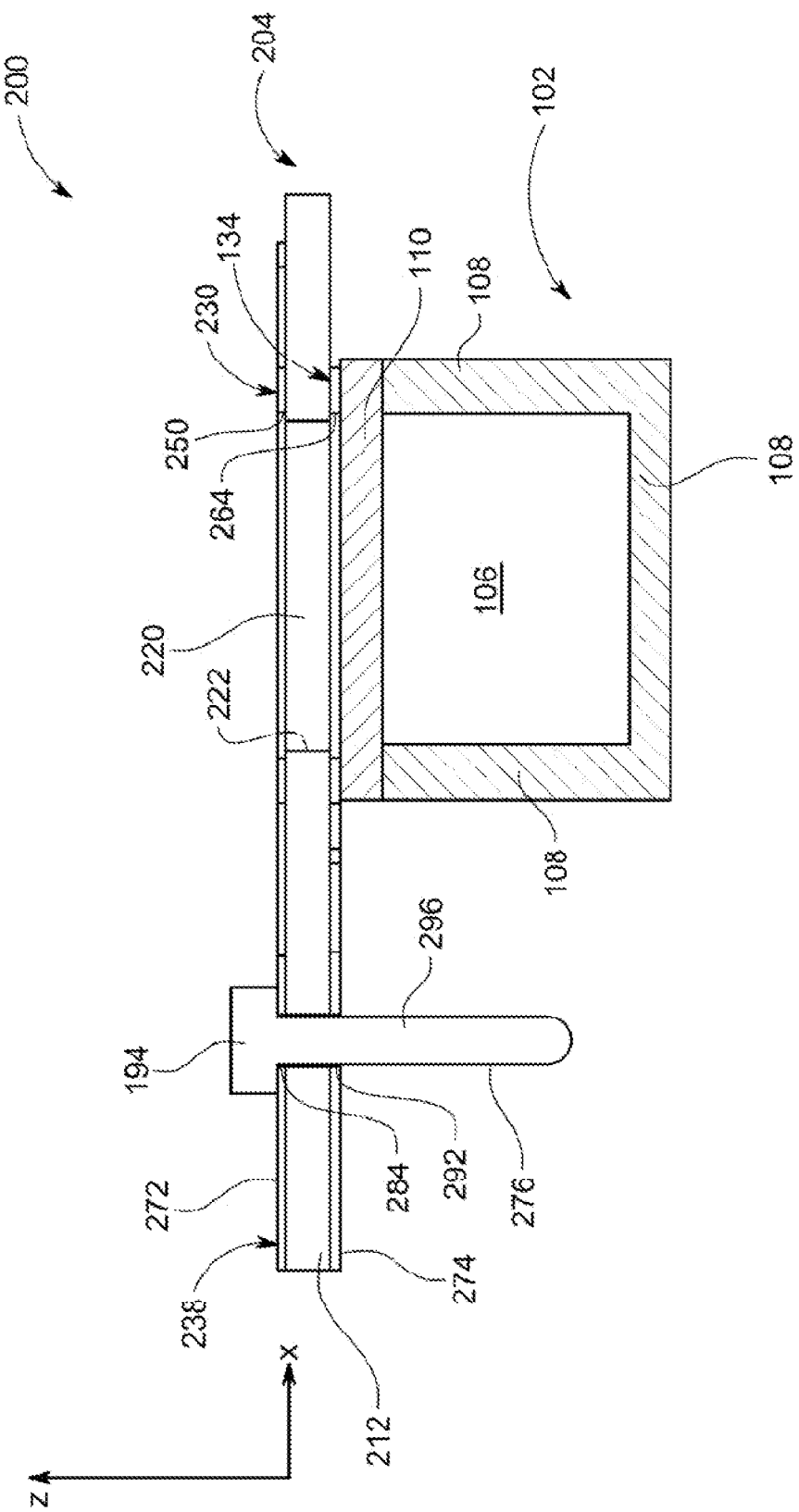
FIG. 12 depicts a cross-sectional view of a photoionization detector including the electrode stack assembly of FIG. 7.
Figure 13:
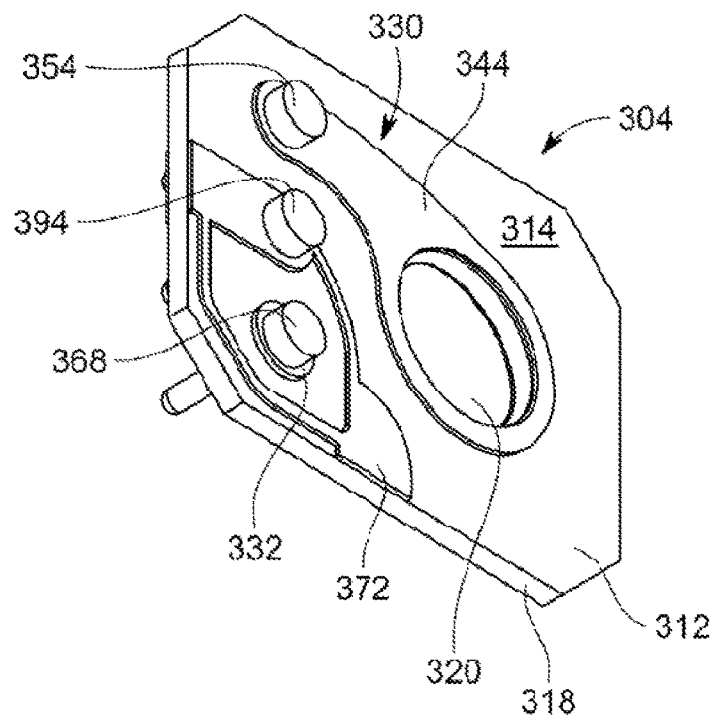
FIG. 13 depicts a top perspective view of an electrode stack assembly according to a second embodiment.
Figure 14:
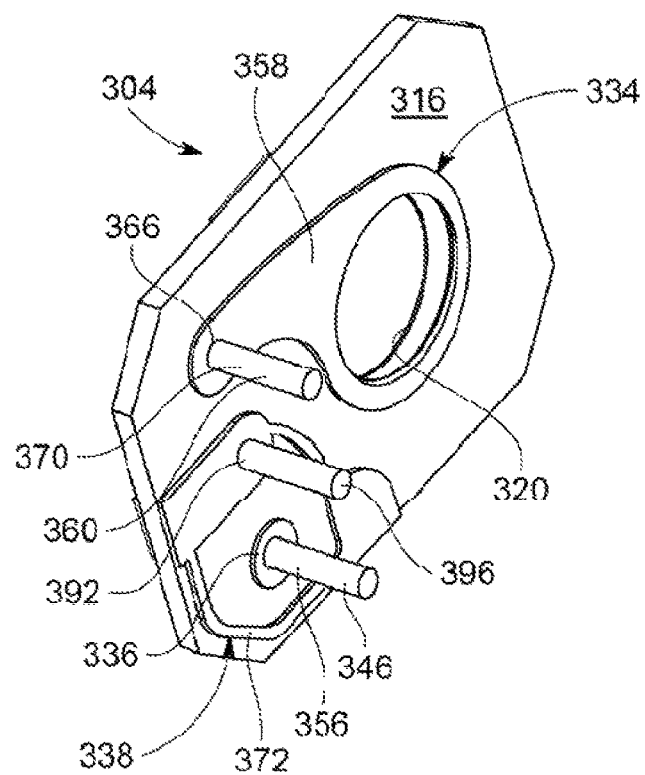
FIG. 14 depicts a bottom perspective view of the electrode stack assembly of FIG. 13.
Figure 15:
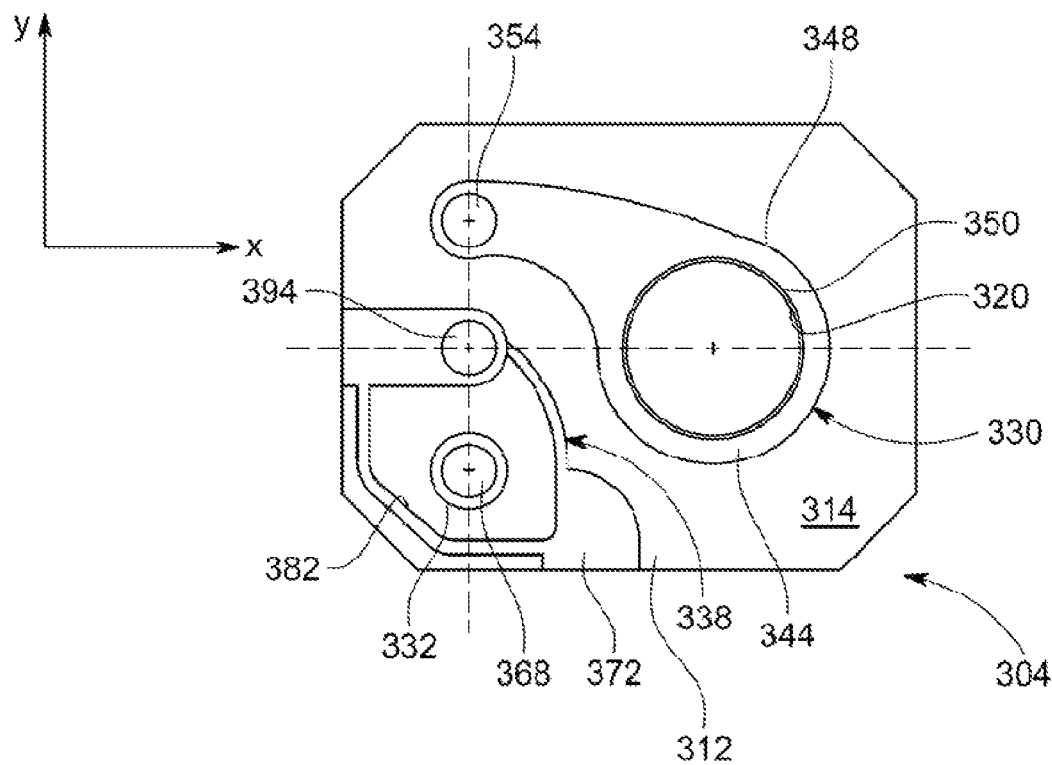
FIG. 15 depicts a top plan view of the electrode stack assembly of FIG. 13.
Figure 16:
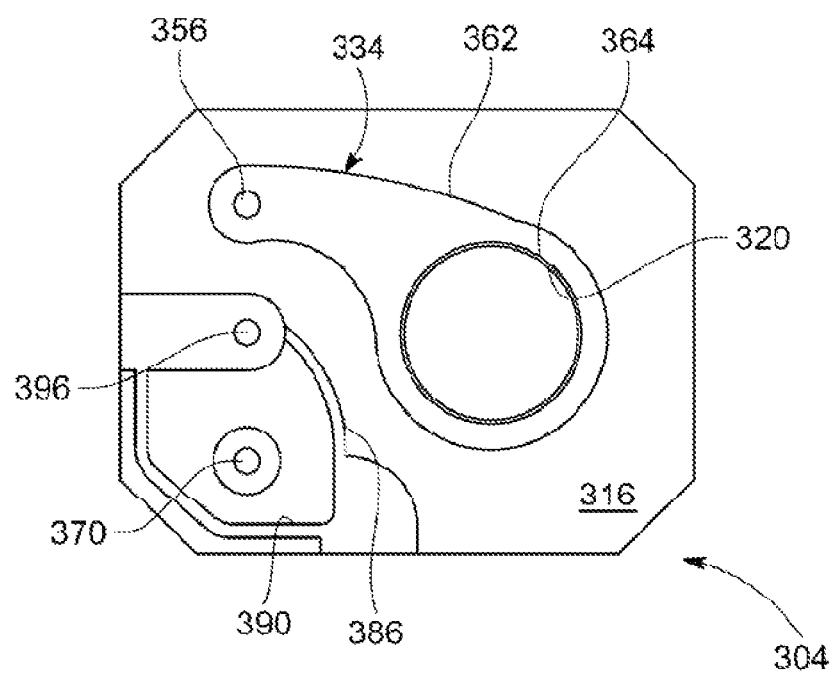
FIG. 16 depicts a bottom plan view of the electrode stack assembly of FIG. 13.
Figure 17:
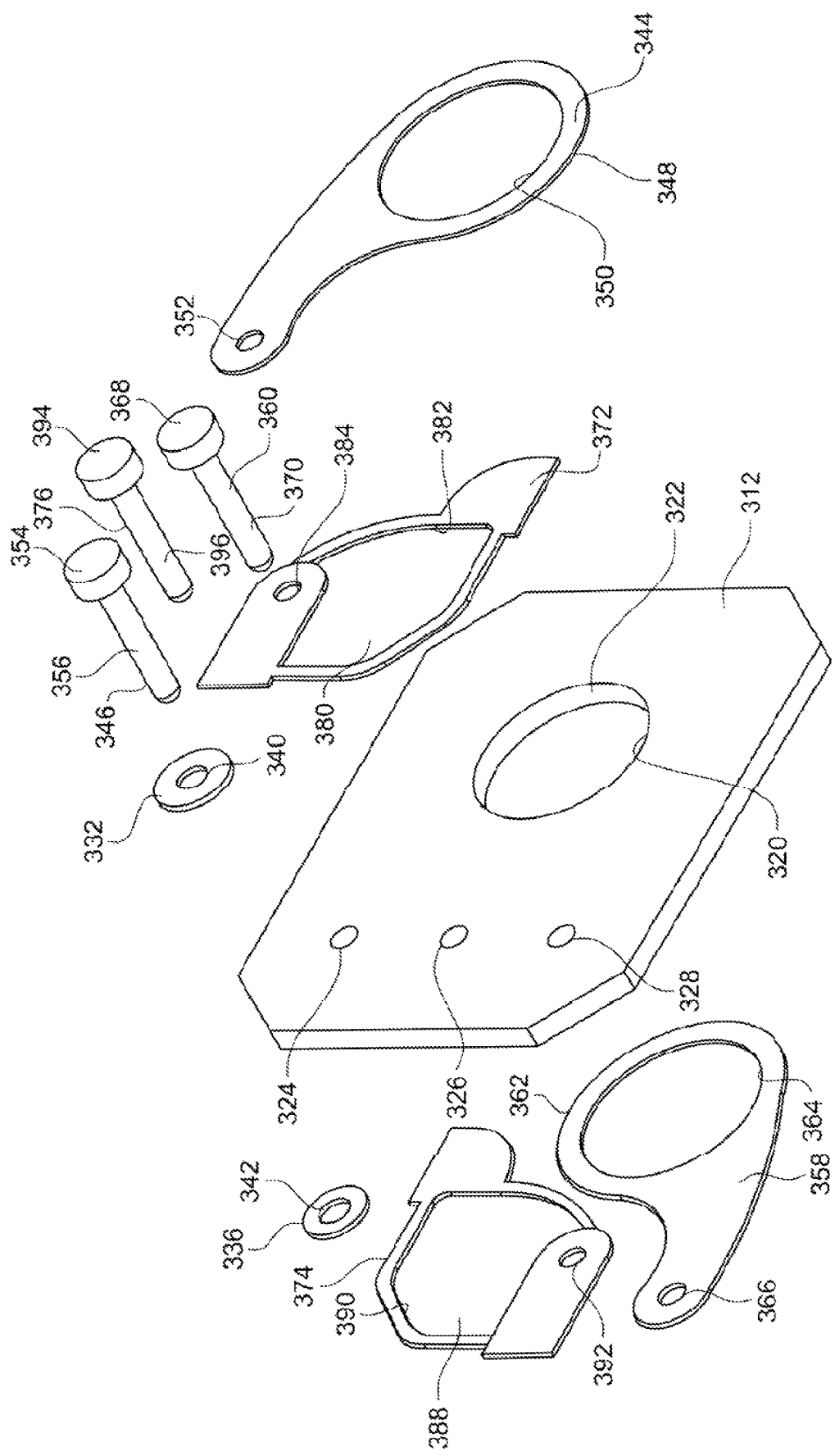
FIG. 17 depicts an exploded perspective view of the electrode stack assembly of FIG. 13.
Figure 18:
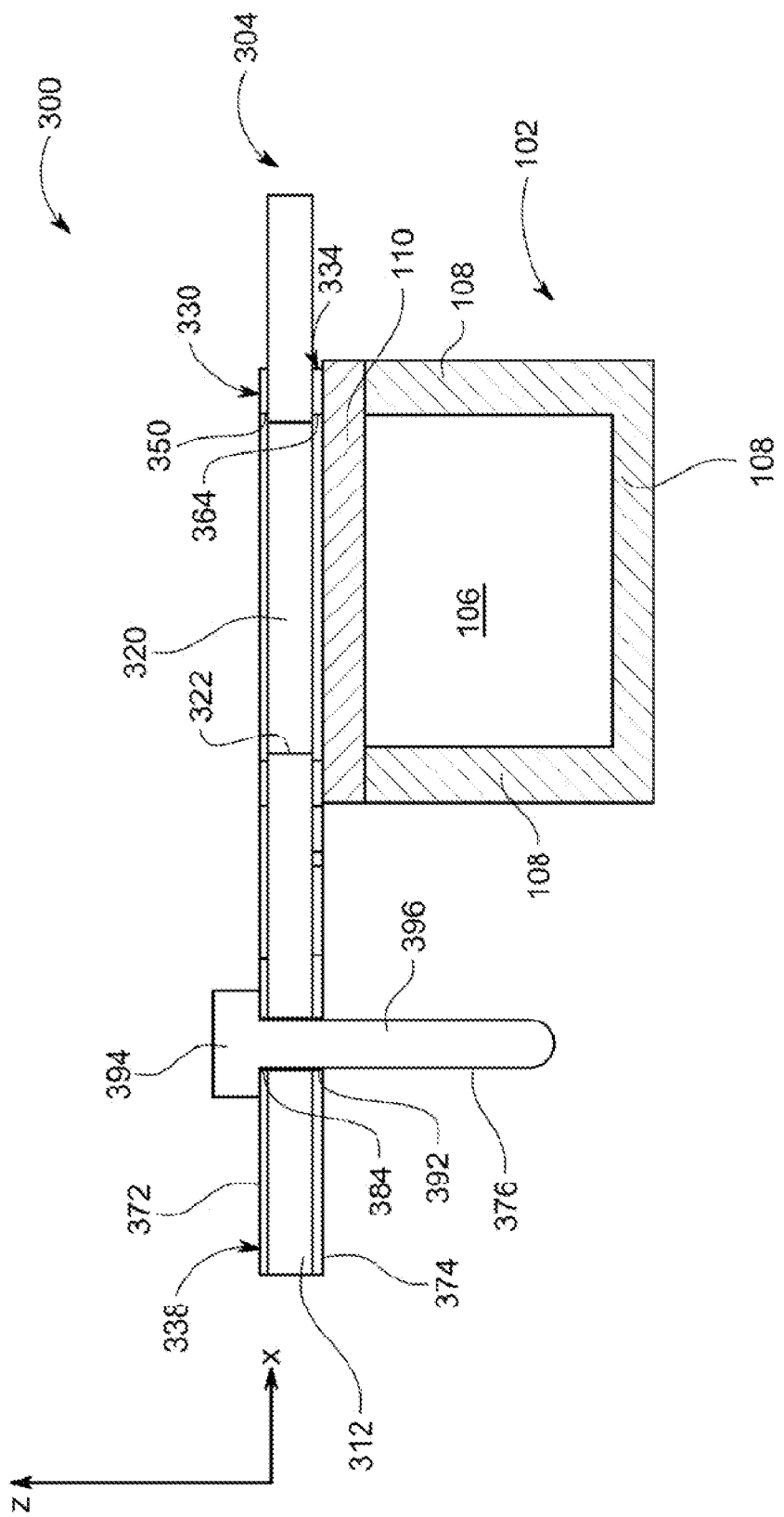
FIG. 18 depicts a cross-sectional view of a photoionization detector including the electrode stack assembly of FIG. 13.

As best illustrated in FIGS. 7 and 9, the top body portion 272 has a top surface, a bottom surface and a continuous outer edge 278 extending between the top and bottom surfaces. An opening 280 formed by a continuous wall 282 and a pin mounting hole 284 are provided through the top body portion 272, are spaced from each other and are spaced from the outer edge 278, and extend from the top surface to the bottom surface. The bottom surface of the top body portion 272 is provided on the top surface 214 of the substrate 212 such that the pin mounting hole 284 is in alignment with the pin mounting hole 224 through the substrate 212. The counter electrode 230 is encircled within, but separated from, the wall 282. The diameter of the pin mounting hole 284 is sized to generally match the diameter of the pin mounting hole 226.

The bottom body portion 274 has a top surface, a bottom surface and a continuous outer edge 286 extending between the top and bottom surfaces. An opening 288 formed by a continuous wall 290 and a pin mounting hole 292 are provided through the bottom body portion 274, are spaced from each other and are spaced from the outer edge 286, and extend from the top surface to the bottom surface. The top surface of the bottom body portion 274 is provided on the bottom surface 216 of the substrate 212 such that the pin mounting hole 292 is in alignment with the pin mounting hole 226 through the substrate 212. The shaft 256 of the pin 246 and bottom contact pad 236 (if provided) are encircled within, but separated from, the wall 290. The pin mounting hole 292 is sized to generally match the diameter of the pin mounting hole 226.

The pin 276 has an enlarged head portion 294 that preferably has an outer diameter that is larger than a diameter of the pin mounting hole 226, and an elongated shaft 296 extending therefrom. The enlarged head portion 294 of the pin 276 rests on the top surface of the top body portion 272, and the shaft 296 extends through the pin mounting hole 284 of the top body portion 272, through the pin mounting hole 226 of the substrate 212, through the pin mounting hole 292 of the bottom body portion 274, and the shaft 296 extends from the bottom surface of the bottom body portion 274. Pin 276 is preferably held in place by known means, e.g., soldering to the top body portion 272 and to the bottom body portion 274.

In use, an electric potential is applied from below the substrate 212 to the pin 246 which applies electric potential to the body 244 of the counter electrode 230 and to the bottom contact pad 236 (if provided), an electric potential is applied from below the substrate 212 to the pin 260 which applies electric potential to the body 258 of the sensing electrode 234 and to the top contact pad 232 (if provided), and an electric potential is applied from below the substrate 212 to the pin 276 which applies electric potential to the top body portion 272 and to the bottom body portion 274. When the PID 200 is operating in block mode, the third electrode 238 is held at or close to (within 20 Volts) the potential of the sensing electrode 234. As a result, the third electrode 238 acts as a guard electrode. In the block mode, the leak current is stopped by the guard electrode 238, and the measured current is considered as the true plasma current, which correlates to the gas concentration. When the PID 200 is operating in compensation mode, the third electrode 238 is held at or close to (within 20 Volts) the potential of the counter electrode 230. As a result, the third electrode 238 acts as an auxiliary electrode. In the compensation mode, the leak current is subtracted from the total current to afford the true plasma current.

The sensing electrode 234 collects the electrons from the ionized gas in the ionization chamber formed by cavity 220. The top body portion 272 electrically separates the pin 260 from the counter electrode 230, and the bottom body portion 274 electrically separates the pin 260 from the counter electrode 230, thereby substantially eliminating the primary pathway of surface leak current. The third electrode 238 separates a current path of the counter electrode 230 from a current path of the sensing electrode 234.

Attention is directed to the third embodiment of the PID 300 shown in FIGS. 13-18. PID 300 includes lamp assembly 102 and an electrode stack assembly 304 which are operatively associated with one another. The PID 300 and the electrode stack assembly 304 are intended to be operated in the block mode or the compensation mode. The lamp assembly 102 of PID 300 is identical to the lamp assembly 102 of PID 100 and, therefore, for brevity purposes, will not be described again in detail.

The electrode stack assembly 304 includes a substrate 312 that is identically formed to the substrate 112, a counter electrode 330 identically formed to the counter electrode 130, an optional top contact pad 332 identically formed to the top contact pad 132, a sensing electrode 334 identically formed to the sensing electrode 134, a bottom contact pad 336 (if provided) identically formed to the bottom contact pad 136 (if provided), and a third electrode 338 which in one mode forms a guard electrode and another mode provides an auxiliary electrode. The counter electrode 330 and top contact pad 332 (if provided) are provided on the top surface 314 of the substrate 312 in an identical manner to that of the first embodiment. Likewise, the sensing electrode 334 and bottom contact pad 336 (if provided) are provided on the bottom surface 316 of the substrate 312 in an identical manner to that of the first embodiment. The pin 346 extends through the body 372 of the counter electrode 330, the substrate 312 and the bottom pad 336 (if provided) in the same manner as the first embodiment, and is coupled to the components in the same manner (or may integrally formed as part of the counter electrode 330). The pin 360 extends through the top contact pad 332 (if provided), the substrate 312, and the body 358 of the sensing electrode 334 in the same manner as the first embodiment, and is coupled to the components in the same manner (or may integrally formed as part of the sensing electrode 334). As such, the specifics are not repeated herein and like element are denoted with like reference numerals in the three hundreds.

The third electrode 338 includes a top body portion 372 and a bottom body portion 374 which are coupled together by a pin 376.

The top body portion 372 has a top surface, a bottom surface and a continuous outer edge 378 extending between the top and bottom surfaces. An opening 380 formed by a continuous wall 382 and a pin mounting hole 384 are provided through the top body portion 372, are spaced from each other and are spaced from the outer edge 378, and extend from the top surface to the bottom surface. The bottom surface of the top body portion 372 is provided on the top surface 314 of the substrate 312 such that the pin mounting hole 384 is in alignment with the pin mounting hole 326 through the substrate 312. The top contact pad 332 (if provided) and the enlarged head portion 368 of the pin 360 are encircled within, but separated from, the wall 382 forming the opening 380. The pin mounting hole 384 is sized to generally match the diameter of the pin mounting hole 326.

The bottom body portion 374 has a top surface, a bottom surface and a continuous outer edge 386 extending between the top and bottom surfaces. An opening 388 formed by a continuous wall 390 and a pin mounting hole 392 are provided through the bottom body portion 374, are spaced from each other and are spaced from the outer edge 386, and extend from the top surface to the bottom surface. The top surface of the bottom body portion 374 is provided on the bottom surface 316 of the substrate 312 such that the pin mounting hole 392 is in alignment with the pin mounting hole 326 through the substrate 312. The shaft 356 of the pin 346 and the bottom contact pad 336 (if provided) are encircled within, but separated from, the wall 390. The pin mounting hole 392 is sized to generally match the diameter of the pin mounting hole 326.

The pin 376 has an enlarged head portion 394 that preferably has an outer diameter that is larger than a diameter of the pin mounting hole 326, and an elongated shaft 396 extending therefrom. The enlarged head portion 394 of the pin 376 rests on the top surface of the top body portion 372, and the shaft 396 extends through the pin mounting hole 384 of the top body portion 372, through the pin mounting hole 326 of the substrate 312, through the pin mounting hole 392 of the bottom body portion 374, and the shaft 396 extends from the bottom surface of the bottom body portion 374. Pin 376 is preferably held in place by known means, e.g., soldering to the top body portion 372 and to the bottom body portion 374.

In use, an electric potential is applied from below the substrate 312 to the pin 346 which applies electric potential to the body 344 of the counter electrode 330 and to the bottom contact pad 336 (if provided), an electric potential is applied from below the substrate 312 to the pin 370 which applies electric potential to the body 358 of the sensing electrode 334 and to the top contact pad 332 (if provided), and an electric potential is applied from below the substrate 312 to the pin 376 which applies electric potential to the top body portion 372 and to the bottom body portion 374. When the PID 300 is operating in block mode, the third electrode 330 is held at or close to (within 20 Volts) the potential of the sensing electrode 334. As a result, the third electrode 330 acts as a guard electrode. In the block mode, the leak current is stopped by the guard electrode 330, and the measured current is considered as the true plasma current, which correlates to the gas concentration. When the PID 300 is operating in compensation mode, the third electrode 330 is held at or close to (within 20 Volts) the potential of the counter electrode 330. As a result, the third electrode 330 acts as an auxiliary electrode. In the compensation mode, the leak current is subtracted from the total current to afford the true plasma current.

The sensing electrode 334 collects the electrons from the ionized gas in the ionization chamber formed by cavity 320. The top body portion 372 electrically separates the pin 360 from the counter electrode 330, and the bottom body portion 374 electrically separates the pin 360 from the counter electrode 330, thereby substantially eliminating the primary pathway of surface leak current. The third electrode 330 separates a current path of the counter electrode 330 from a current path of the sensing electrode 334.

In each embodiment, a filter material (not shown) may be applied to cover the opening 180, 280, 380 to prevent dust particles from entering through the top end of the cavity 120, 220, 320.

While the lamp assembly 102 is shown abutting against the sensing electrode 134, 234, 334, the lamp assembly 102 may be spaced from the sensing electrode 134, 234, 334. While the lamp assembly 102 is shown below the electrode stack assembly 104, 204, 304, it is to be understood that the PID 100, 200, 300 can be inverted and the lamp assembly 102 be provided above the electrode stack assembly 104, 204, 304. The PID 100, 200, 300 can also be placed on its side such that the lamp assembly 102 is to the left and the electrode stack assembly 104, 204, 304 is to the right, or vice versa.

While the pin mounting holes 124, 126, 128, 224, 226, 228, 324, 326, 328, 140, 240, 340, 142, 242, 342, 152, 252, 352, 166, 266, 366, 192, 292, 392 are described and shown herein as having a diameter, the pin mounting holes are not limited to a circular cross-section. The pin mounting holes can be multi-sides such as square, triangular, etc. While the openings 150, 250, 350, 164, 264, 364 and the cavity 120, 220, 320 are described and shown herein as having a diameter, the openings 150, 250, 350, 164, 264, 364 and the cavity 120, 220, 320 are not limited to a circular cross-section. The openings and the cavity can be multi-sides such as square, triangular, etc.

While particular embodiments are illustrated in and described with respect to the drawings, it is envisioned that those skilled in the art may devise various modifications without departing from the spirit and scope of the appended claims. It will therefore be appreciated that the scope of the disclosure and the appended claims is not limited to the specific embodiments illustrated in and discussed with respect to the drawings and that modifications and other embodiments are intended to be included within the scope of the disclosure and appended drawings. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure and the appended claims.

We claim:

1. A method of operating a photoionization detector, the method comprising:
   applying a first electric potential to a counter electrode on a top surface of an electrically insulative substrate;
   applying a second electric potential to a sensing electrode on a bottom surface of the electrically insulative substrate;
   applying a third electric potential to a third electrode having a pin mounting hole positioned for a first pin to pass therethrough the substrate and electrically separate the sensing electrode from the counter electrode; and
   causing ionization of gas in a cavity of the electrically insulative substrate.

2. The method of claim 1, wherein the applying the third electrical potential to the third electrode comprises encircling a second pin of the sensing electrode with a top body portion of the third electrode, and spacing therefrom, and encircling a body of the sensing electrode with a bottom body portion of the third electrode, and spacing therefrom.

3. The method of claim 1, wherein the applying the third electrical potential to the third electrode comprises encircling a body of the counter electrode with a top body portion of the third electrode, and spacing therefrom, and encircling a second pin of the sensing electrode with a bottom body portion of the third electrode, and spacing therefrom.

4. The method of claim 1, wherein the applying the third electrical potential to the third electrode comprises encircling a second pin of the sensing electrode with a top body portion of the third electrode, and spacing therefrom, encircling a third pin of the counter electrode with a bottom body portion of the third electrode, and spacing therefrom.

5. The method of claim 1, further comprising extending an elongated shaft having an enlarged head from a third pin of the counter electrode and a second pin of the sensing electrode, extending the shafts through the substrate, resting the enlarged head of the third pin of the counter electrode on a body of the counter electrode and electrically coupling thereto, placing the enlarged head of the second pin of the sensing electrode above the substrate, and electrically coupling the shaft of the second pin of the sensing electrode to the sensing electrode.

6. The method of claim 1, further comprising extending pins of the counter electrode and the sensing electrode through pin mounting holes in the substrate with each pin mounting hole having a diameter which is larger than a diameter of shafts of the pins of the counter electrode and the sensing electrode.

7. The method of claim 6, further comprising aligning centers of the pin mounting holes with each other in a first direction, and aligning a center of a pin mounting hole in which the first pin is mounted and a center of the cavity in a second direction.

8. The method of claim 1, further comprising configuring a lamp assembly in combination with the counter, sensing, and third electrodes to ionize gas within the cavity.

9. The method of claim 1, wherein the photoionization detector comprises an opening therethrough a top body portion of the third electrode extending from a top surface thereof to a bottom surface thereof, and an opening therethrough a bottom body portion of the third electrode extending from a top surface thereof to a bottom surface thereof.

10. The method of claim 1, further comprising including a top contact pad on the top surface of the substrate, and extending a second pin of the sensing electrode through the top contact pad.

11. The method of claim 1, further comprising including a bottom contact pad on the bottom surface of the substrate, and extending a third pin of the counter electrode through the bottom contact pad.

12. A method of operating a photoionization detector in compensation mode, the method comprising:
    applying a first electric potential to a counter electrode on a top surface of an electrically insulative substrate;
    applying a second electric potential to a sensing electrode on a bottom surface of the insulative substrate;
    applying a third electric potential to a third electrode having a pin passing through the substrate and separating a current path of the counter electrode from a current path of the sensing electrode, wherein the first and third electric potentials are the same or generally the same, and the second electric potential is generally higher than the first potential; and
    causing ionization of gas in a cavity of the insulative substrate.

13. The method of claim 12, wherein the applying the third electrical potential comprises holding the third electrical potential at or close to the first electric potential of the counter electrode.

14. The method of claim 12, further comprising measuring a leak current between the counter electrode and sensing electrode using the third electrode, wherein the third electrode is an auxiliary electrode.

15. The method of claim 14, further comprising measuring a measured current between the counter electrode and sensing electrode.

16. The method of claim 15, further comprising subtracting the leak current from the measured current to calculate a true plasma current.

17. A method of operating a photoionization detector in a block mode, the method comprising:
    applying a first electric potential to a counter electrode on a top surface of an electrically insulative substrate;
    applying a second electric potential to a sensing electrode on a bottom surface of the insulative substrate;
    applying a third electric potential to a third electrode having a pin passing through the substrate and separating a current path of the counter electrode from a current path of the sensing electrode, wherein the second and third electric potentials are the same, and the second electric potential is generally higher than the first potential; and causing ionization of gas in a cavity of the insulative substrate.

18. The method of claim 17, wherein the applying the third electrical potential comprises holding the third electrical potential at or close to the second electric potential of the sensing electrode.

19. The method of claim 17, further comprising blocking a leak current between the counter electrode and sensing electrode using the third electrode, wherein the third electrode is a guard electrode.

20. The method of claim 19, further comprising measuring a measured current between the counter electrode and sensing electrode to calculate a true plasma current.

* * * * *